(12) United States Patent
Valsecchi et al.

(10) Patent No.: US 9,890,186 B2
(45) Date of Patent: Feb. 13, 2018

(54) METHOD OF MANUFACTURING CYCLOPHOSPHAZENE DERIVATIVES

(71) Applicant: SOLVAY SPECIALTY POLYMERS ITALY S.P.A., Bollate (IT)

(72) Inventors: Roberto Valsecchi, Osio Sopra (IT); Rosaldo Picozzi, Cesate (IT); Pier Antonio Guarda, Arese (IT)

(73) Assignee: SOLVAY SPECIALTY POLYMERS ITALY S.P.A., Bollate (Milan) (IT)

( * ) Notice: Subject to any disclaimer, the term of this patent is extended or adjusted under 35 U.S.C. 154(b) by 0 days.

(21) Appl. No.: 14/896,048

(22) PCT Filed: Jun. 3, 2014

(86) PCT No.: PCT/EP2014/061462
§ 371 (c)(1),
(2) Date: Dec. 4, 2015

(87) PCT Pub. No.: WO2014/195299
PCT Pub. Date: Dec. 11, 2014

(65) Prior Publication Data
US 2016/0130289 A1    May 12, 2016

(30) Foreign Application Priority Data

Jun. 6, 2013 (EP) .................... 13170913

(51) Int. Cl.
| | |
|---|---|
| C07F 9/6593 | (2006.01) |
| C07F 9/6581 | (2006.01) |
| G11B 5/725 | (2006.01) |
| C10M 105/74 | (2006.01) |
| C08G 65/00 | (2006.01) |
| C08G 65/335 | (2006.01) |
| C08G 65/337 | (2006.01) |

(52) U.S. Cl.
CPC ...... C07F 9/65815 (2013.01); C07F 9/65812 (2013.01); C07F 9/65817 (2013.01); C08G 65/007 (2013.01); C08G 65/337 (2013.01); C08G 65/3356 (2013.01); C10M 105/74 (2013.01); G11B 5/725 (2013.01)

(58) Field of Classification Search
CPC .............. C07F 9/65815; C07F 9/65817; C07F 9/65812; C08G 65/007; C08G 65/337; C08G 65/3356; C10M 105/74; G11B 5/725
See application file for complete search history.

(56) References Cited

U.S. PATENT DOCUMENTS

| | | |
|---|---|---|
| 2002/0183211 A1 | 12/2002 | Akada et al. |
| 2008/0020171 A1 | 1/2008 | Wakabayashi et al. |
| 2008/0305975 A1 | 12/2008 | Liu et al. |
| 2009/0318664 A1 | 12/2009 | Yang et al. |
| 2012/0251843 A1* | 10/2012 | Yan ........................ G11B 5/725 428/800 |
| 2012/0276417 A1 | 11/2012 | Shimokawa et al. |

FOREIGN PATENT DOCUMENTS

| | | | |
|---|---|---|---|
| CN | 101506219 A1 | 8/2009 | |
| WO | 2007043450 A1 | 4/2007 | |
| WO | WO 2007043450 A1 * | 4/2007 | .......... C07F 9/65815 |
| WO | 2008/000706 A1 | 1/2008 | |

(Continued)

OTHER PUBLICATIONS

Kang H.H. et al., "The Use of Cyclic Phosphazene Additives to Enhance the Performance of the Head/Disk Interface", Lubrication Engineering (Journal of the Society of Tribologists and Lubrication Engineers), Mar. 1999, vol. 55(3), p. 22-27.

Allcock H.R. et al, "Phosphonitrilic Compounds. IV. Preparation and Polymerization of Allylaminophosphonitrile Compounds" Journal Organic Chemistry, 1965, vol. 30(3), p. 947-949.

Lee S.B. et al., "Thermosensitive Cyclotriphosphazenes", J. Am. Chem. Soc., 2000, vol. 122(34), p. 8315-8316—American Chemical Society.

Veldboer K. et al., "Liquid chromatography/electrospray time-of-flight mass spectrometry for the characterisation of cyclic phosphazenes", Rapid Commun. Mass Spectrom., 2011, vol. 25, p. 147-154—John Wiley & Sons, Ltd.

(Continued)

Primary Examiner — Taiwo Oladapo

(57) ABSTRACT

A method of manufacturing cyclophosphazenes PFPE derivatives to be used in the lubrication of magnetic recording media is herein provided. The method comprises: a) a (per)fluoropolyether (PFPE) polyol [PFPE ($P_{pol}$)] comprising a fluoropolyoxyalkylene chain ($R_f$) having two chain ends, each chain end comprising at least one hydroxy group, and b) the corresponding alkoxide of perfluoropolyether ($P_{pol}$) [PFPE ($P_{alk}$)] wherein the equivalent concentration of PFPE ($P_{alk}$) in PFPE ($P_{pol}$) is lower than 30%, preferably ranging from 5% to 15%; 2) contacting mixture (M) with a perhalocyclophosphazene ($CP_{halo}$) to provide a mixture (M1) containing an equivalent ratio of PFPE ($P_{alk}$)/($CP_{halo}$) of at least 1; 3) allowing mixture (M1) to react until complete disappearance of P—Cl groups to provide a mixture (M2); 4) submitting mixture (M2) to hydrolysis to provide a mixture (M3); 5) optionally removing ($P_{pol}$) from mixture (M3) to provide a mixture (M4). A method of purifying mixture (M4) is also herein provided.

15 Claims, No Drawings

(56) References Cited

FOREIGN PATENT DOCUMENTS

WO     WO 2008000706 A1 *   1/2008   .......... C07F 9/65815
WO          2009043928 A1     4/2009

OTHER PUBLICATIONS

Anil E.J. et al., "Chemistry of diphenyltetrafluorophosphazene: Reactions with dilithiated diols", Journal of Fluorine Chemistry, 2006, vol. 127(8), p. 1046-1053—Elsevier B.V.

* cited by examiner

METHOD OF MANUFACTURING CYCLOPHOSPHAZENE DERIVATIVES

CROSS-REFERENCE TO RELATED APPLICATIONS

This application is a U.S. national stage entry under 35 U.S.C. § 371 of International Application No. PCT/EP2014/061462 filed Jun. 3, 2014, which claims priority to European application No. 13170913.1, filed on Jun. 6, 2013. The entire contents of these applications are explicitly incorporated herein by this reference.

TECHNICAL FIELD

The present invention relates to a method for manufacturing and purifying certain (per)fluororopolyether cyclophosphazene derivatives to be used as lubricants for sliding or moving parts of magnetic recording media (MRM).

BACKGROUND ART (Per)fluoropolyethers (PFPEs) and derivatives thereof are currently used in the lubrication of MRM, namely in the lubrication of sliding or moving parts of such media. In particular certain PFPE derivatives containing a PFPE chain having terminal and non-terminal polar functional groups have shown best performances; indeed, thanks to the high chemical stability of the PFPE chain and to the presence of polar functional groups, such derivatives are able to form an even, long-lasting lubricant film on the surface of the moving parts of MRM. In particular, magnetic disk drives surfaces are usually coated with a carbon overcoat to which polar functional groups ensure adhesion, thereby preventing the lubricant film from being spun off during revolution of the disk.

Examples of the above PFPE derivatives are those containing at least one phosphazene cyclic group and at least one PFPE chain bearing one or more hydroxy groups. The phosphazene cyclic group is highly stable from the thermal standpoint and further increases the stability of the PFPE chain; without being bound to theory, it is believed that the phosphazene ring acts as a Lewis base which counteracts the catalytic effect on thermal degradation of the PFPE due to the Lewis acids typically present as impurities in the MRM. KANG, H. J., et al. The Use of Cyclic Phosphazene Additives to Enchance the Performance of the Head/Disk Interface. *Journal of the Society of Tribologists and Lubrication Engineering*. March 199, p. 22-27. Instead, the one or more hydroxy groups ensure adherence to MRM surfaces.

Certain patent documents, including US 2002183211 A (AKADA TAMIO ET AL) 5 Dec. 2002, US 2008020171 A (MATSUMURA OIL RES CORP [JP]) 26 Jan. 2006, US 2008020171 A (MATSUMURA OIL RES CORP [JP]) 26 Jan. 2006, US 2008305975 A (SEAGATE TECHNOLOGY LLC [US]) 11 Dec. 2008, WO 2007/043450 (MATSUMURA OIL RES CORP [JP]) 19 Apr. 2007 and US 2012276417 A (WD MEDIA SINGAPORE PTE LTD [US]) 27 Jan. 2011 disclose lubricants for magnetic recording media containing at least one phosphazene cyclic group bearing at least one optionally substituted phenoxy group and at least one hydroxy-substituted perfluoropolyether chain.

However, it has been observed that the optionally substituted phenoxy group on the phosphazene ring might reduce the mobility of the lubricant and decrease the durability of the MRM. Thus, it would be desirable to provide PFPE phosphazene derivatives for the lubrication of MRM, which do not show this drawback; in particular, it would be desirable to provide PFPE cyclophosphazene derivatives wherein each phosphorous atom bears a PFPE chain having at least one —OH group.

US 2012251843 A (SEAGATE TECHNOLOGY LLC [US]) 4 Oct. 2012 discloses, inter alia, a composition comprising a central core comprising a cyclic group, including a cyclotriphosphazene, and six arms extending from the central core, wherein each arm comprises a PFPE or a PFPE derivative. The PFPE derivative can be a PFPE chain having one or more terminal groups including: —CH$_2$OH, —OCH$_2$CH$_2$OH, —CH$_2$CH(OH)CH$_2$OH, —CH$_2$CH(OH)CH$_3$ and —OCH$_2$CH$_2$CH$_2$OH. The PFPE derivative can also have non-terminal functional groups including —CH$_2$CH(OH)CH$_2$—, —CH(OH)CH(OH)CH$_2$—, —CH$_2$CH(OH)CH$_2$CH(OH)CH$_2$—, —CH(CH$_2$OH)— and —CH(OH)CH(OH)CH$_2$—. In particular, FIG. 7 illustrates a hexacyclophosphazene wherein each phosphorous atom bears two PFPE substituents of formula:

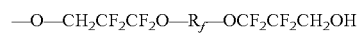

wherein R$_f$ is (CF$_2$CF$_2$CF$_2$O)$_n$ with n equal to or higher than 3.

However, US 2012251843 does not teach how to manufacture the claimed composition.

US 2009318664 (SEAGATE TECHNOLOGY LLC) 24 Dec. 2009 discloses compounds comprising a backbone with a PFPE chain, wherein one or more cyclophosphazene rings is attached to or incorporated in the chain, and at least two functional groups attached either to the backbone or to the cyclophosphazene ring or both. This document reports one synthesis example disclosing the reaction of a compound referred to as A20H, having formula:

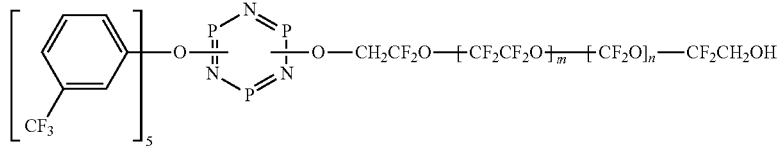

with epichlorohydrin, to provide and intermediate which is in turn reacted with a solution obtained after heating 6.7 mmol Fomblin® Z-DOL PFPE with 6.7 mmol potassium hydroxide in about 0.2 ml water. Therefore, in such solution, 50% of the hydroxyl groups equivalents of Fomblin® Z-DOL PFPE is in the salified form. This document does not contain examples teaching the synthesis of phosphazenes substituted with more than one PFPE chain, each chain bearing at least one hydroxyl group.

The synthesis of hexasubstituted cyclotriphosphazenes by reaction of a nucleophile (e.g. an amine, an alcohol or a phenol) with hexachlorophosphazenes is reported in the literature, for example in: ALLCOCK, H. R., et al. Phosphonitrilic Compounds. IV. Preparation and Polymerization of Allylaminophosphonitrile Compounds1,2. *Journal Organic Chemistry.* 1965, vol. 30, no. 3, p. 947-949. and in LEE, S. B., et al. Thermosensitive Cyclotriphosphazenes. *J. Am. Chem. Soc.* 2000, vol. 122, no. 34, p. 8315-8316. When the nucleophile is an alcohol or a phenol the corresponding alkaline metal alkoxide or phenoxide is required in order to accomplish the nucleophile substitution on the phosphorous atoms.

Reactions of chloro- or fluoro-cyclophosphazenes with alkoxides of aliphatic diols, for example with dilithiated propanediol, are also reported in the literature, for example in:

VELDBOER, K., et al. Liquid chromatography/elctrospray time-of-flight mass spectrometry for the characterisation of cyclic phosphazenes. *Rapid Commun. Mass Spectrom.* 2011, vol. 25, p. 147-154.

ANIL, Elias J., et al. Chemistry of diphenyltetrafluorophosphazene: Reactions with dilithiated diols. *Journal of Fluorine Chemistry.* 2006, vol. 127, no. 8, p. 1046-1053.

In greater detail, Anil et al., investigates on the reaction of gem-diphenyltetrafluorophosphazene $[1,1-(C_6H_5)_2]P_3N_3F_4$ of formula:

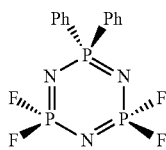

with dilithiated propanediol $LiO(CH_2)_3OLi$.

This reaction gives rise to complex product mixtures, typically containing four products:

a) spiro-$\{3,3-[O(CH_2)_3O]\}[1,1-(C_6H_5)_2]P_3N_3F_2$, having formula:

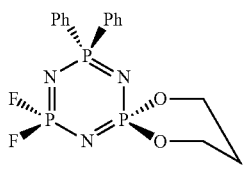

b) ansa-$\{3,5-[O(CH_2)_3O]\}[1,1-(C_6H_5)_2]P_3N_3F_2$, having formula:

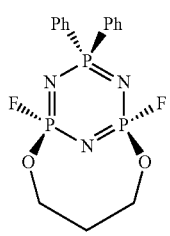

c) bridged-$[N_3P_3F_3(C_6H_5)_2][O(CH_2)_3O]N_3P_3F_3(C_6H_5)_2]$, having formula:

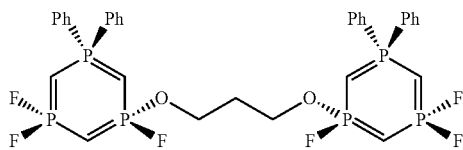

and d) dangling-$[HO(CH_2)_3O](C_6H_5)_2P_3N_3F_3$, having formula:

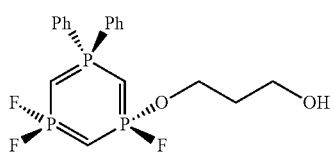

In particular, at par. 4.3.1. of the experimental section, Anil et al. states that when pure dilithiated propanediol is used in the reaction, the resulting mixture contains 39% wt dangling-$[HO(CH_2)_3O](C_6H_5)_2P_3N_3F_3$, 10% wt bridged-$[N_3P_3F_3(C_6H_5)_2][O(CH_2)_3O]N_3P_3F_3(C_6H_5)_2]$ and also 5% wt and 9% wt of the ansa- and spiro-products. At paragraph 4.3.2 of the experimental section, Anil et al. further teaches that a much higher amount of dangling-$[HO(CH_2)_3O](C_6H_5)_2P_3N_3F_3$ (71% wt), and only traces of spiro-, ansa- and bridged-products can be obtained using monolithiated 1,3-propanediol.

When the applicant tried to manufacture hexasubstituted PFPE phosphazene derivatives claimed in US 2012251843 by treatment of a perhalocyclophosphazene with a PFPE diol in accordance with the teaching of Anil et al., unsatisfactory results were obtained using a PFPE diol containing ≥50% wt of the corresponding alkoxide (i.e. a PFPE diol wherein at least one equivalent of alcohol groups was salified); indeed, the desired "dangling" phosphazene derivative, which can be schematically represented by the formula (1) here below:

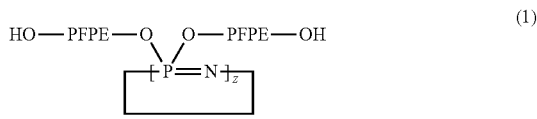

wherein PFPE represents a (per)fluoropolyether chain and z represents an integer of 3 or more was not only obtained in admixture with ansa-, spiro- and bridged-PFPE phosphazenes, which can be schematically respectively represented by formulae (2)-(4) below:

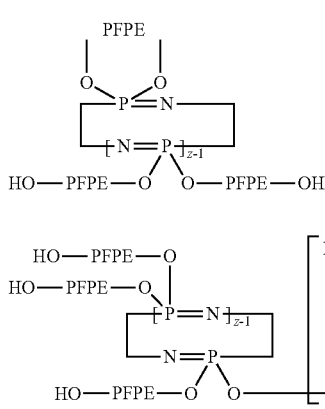
(2)

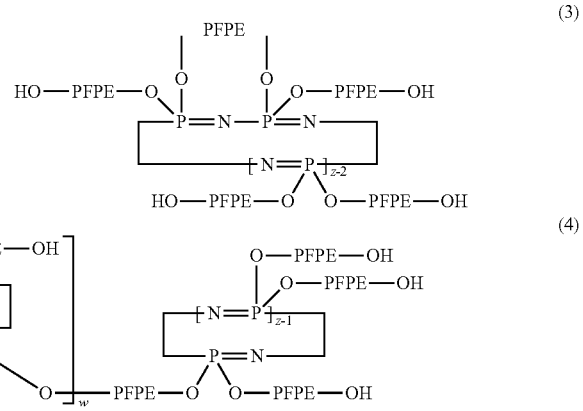
(3)

(4)

wherein PFPE and z are as defined above and w is selected from 0, 1 or 2,
but the amount of bridged-PFPE phosphazene was relevant, usually higher than 50% wt, which resulted in multimodal molecular weight distributions thus increasing the polydispersity of the final product. Since narrow molecular weight distribution is an important requirement for MRM lubricants, the need was felt to provide a convenient method for the manufacture of PFPE phosphazene derivatives comprising a cyclic phosphazene wherein each phosphorus atom of the cyclic phosphazene bears two PFPE substituents, each one containing a PFPE chain having a chain end comprising at least one hydroxy group, said PFPE derivatives having a narrow molecular weight distribution.

SUMMARY OF INVENTION

The applicant has now found out that the above need is met by a method comprising, preferably consisting of, the following steps:
1) providing a mixture (M) containing:
   a) a (per)fluoropolyether (PFPE) polyol [PFPE ($P_{pol}$)] comprising a fluoropolyoxyalkylene chain ($R_f$) having two chain ends, each chain end comprising at least one hydroxy group, and b) the corresponding alkoxide of perfluoropolyether ($P_{pol}$) [PFPE ($P_{alk}$)], wherein the equivalent concentration of PFPE ($P_{alk}$) in PFPE ($P_{pol}$) is lower than 30%, preferably ranging from 5% to 15%;
2) contacting mixture (M) with a perhalocyclophosphazene ($CP_{halo}$) to provide a mixture (M1) containing an equivalent ratio of PFPE ($P_{alk}$)/($CP_{halo}$) of at least 1;
3) allowing mixture (M1) to react until complete disappearance of P—Cl groups to provide a mixture (M2);
4) submitting mixture (M2) to hydrolysis to provide a mixture (M3);
5) optionally removing ($P_{pol}$) from mixture (M3) to provide a mixture (M4).

Mixtures (M2)-(M4) comprise a PFPE cyclophosphazene derivative [PFPE (CP-1)] wherein each phosphorus atom of the phosphazene ring bears two PFPE substituents, each one containing a PFPE chain having a chain end comprising at least one hydroxy group. In the present description, PFPE (CP-1) is otherwise referred to as "dangling PFPE (CP-1)". PFPE (CP-1) can be represented with the above formula (1). Mixtures (M2)-(M4) further contain spiro-, ansa- and bridged-derivatives, in the present description otherwise respectively referred to as PFPE (CP-2)-(CP-4); PFPE (CP-2)-(CP-4) can be represented with the above formulae (2)-(4). However, it has been observed that, thanks to the use of a PFPE mixture (M) wherein the equivalent concentration of PFPE ($P_{alk}$) is lower than 30% (i.e. higher than 0 but lower than 30%), the content of bridged derivatives is usually lower than about 40% wt respect to dangling-, spiro- and ansa-derivatives.

Definitions

In the present description, the indeterminative article "a" is intended to mean "one or more", unless indicated otherwise; when ranges are indicated, range extremes are included, unless indicated otherwise.

Definition of Fluoropolyoxyalkylene Chain

In the present description, a fluoropolyoxyalkylene chain ($R_f$) is a fully or partially fluorinated polyoxyalkylene chain; preferably, chain ($R_f$) comprises repeating units $R°$, said repeating units being chosen among the group consisting of:
(i) —CFXO—, wherein X is F or $CF_3$,
(ii) —CFXCFXO—, wherein X, equal or different at each occurrence, is F or $CF_3$, with the provision that at least one of X is —F,
(iii) —$CF_2CF_2CW_2O$—, wherein each of W, equal or different from each other, are F, Cl, H,
(iv) —$CF_2CF_2CF_2CF_2O$—,
(v) —$(CF_2)_j$—CFZ—O— wherein j is an integer from 0 to 3 and Z is a group of general formula —$OR_f'T_3$, wherein $R_f'$ is a fluoropolyoxyalkene chain comprising a number of repeating units from 0 to 10, said recurring units being chosen among the followings: —CFXO—, —$CF_2CFXO$—, —$CF_2CF_2CF_2O$—, —$CF_2CF_2CF_2CF_2O$—, with each of each of X being independently F or $CF_3$ and $T_3$ being a $C_1$-$C_3$ perfluoroalkyl group.

Definition of (Per)Fluoropolyether

The prefix "(per)" in the term "(per)fluoropolyether" means that the fluoropolyoxyalkylene chain ($R_f$) in the fluoropolyether is fully or partially fluorinated. The acronym "PFPE" stands for (per)fluoropolyether and, when used as substantive, is intended to mean either the singular or the plural form, depending on the context.

Definition of Chain End Comprising at Least One Hydroxy Group

In the present description, a "chain end comprising at least one hydroxy group" is intended to mean a hydrocarbon group containing at least one hydroxy group, said hydrocarbon group being optionally fluorinated and/or optionally containing one or more heteroatoms. Representative examples of such groups include:

—CFXCH$_2$O(CH$_2$CH$_2$O)$_n$H, —CFXCH$_2$O(CH$_2$CHCH$_3$O)$_n$H and —CF$_2$CF$_2$CH$_2$O(CH$_2$CH$_2$O)$_n$H, wherein X is F or CF$_3$ and n ranges from 0 to 5; —CFXCH$_2$O(CH$_2$CHOHCH$_2$O)$_{n'}$H and —CF$_2$CF$_2$CH$_2$O(CH$_2$CHOHCH$_2$O)$_{n'}$H wherein X is F or CF$_3$ and n' ranges from 1 to 3.

The at least one hydroxy group on the chain end is herein after otherwise referred to as "terminal hydroxy group".

Preferred per Fluoropolyether Polyols (P$_{pol}$)

Preferred PFPE (P$_{pol}$) according to the present invention comply with the following formula (II):

(II)

wherein R$_f$ is a fluoropolyoxyalkylene chain as defined above and Y and Y', equal to or different from one another, represent a hydrocarbon group containing at least one hydroxy group, said hydrocarbon group being optionally fluorinated and/or optionally containing one or more heteroatoms.

In formula (II), preferred groups Y and Y' are —CFXCH$_2$O(CH$_2$CH$_2$O)$_n$H, —CFXCH$_2$O(CH$_2$CHCH$_3$O)$_n$H and —CF$_2$CF$_2$CH$_2$O(CH$_2$CH$_2$O)$_n$H, —CFXCH$_2$O(CH$_2$CHOHCH$_2$O)$_{n'}$H and —CF$_2$CF$_2$CH$_2$O(CH$_2$CHOHCH$_2$O)$_{n'}$H, wherein X, n and n' are as defined above.

Preferably, chain R$_f$ complies with the following formula:

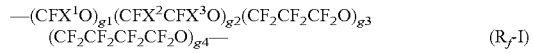
(R$_f$-I)

wherein
X$^1$, X$^2$, X$^3$ equal or different from each other and at each occurrence are independently —F, —CF$_3$;
g1, g2, g3, and g4, equal or different from each other, are independently integers≥0, such that g1+g2+g3+g4 is in the range from 2 to 300, preferably from 2 to 100; should at least two of g1, g2, g3 and g4 be different from zero, the different recurring units are generally statistically distributed along the chain.

Still more preferably, chain R$_f$ is selected from chains of formula:

—(CF$_2$CF$_2$O)$_{a1}$(CF$_2$O)$_{a2}$— (R$_f$-IIA)

wherein:
a1 and a2 are independently integers≥0 such that the number average molecular weight is between 400 and 10,000, preferably between 400 and 5,000; both a1 and a2 are preferably different from zero, with the ratio a1/a2 being preferably comprised between 0.1 and 10;

—(CF$_2$CF$_2$O)$_{b1}$(CF$_2$O)$_{b2}$(CF(CF$_3$)O)$_{b3}$(CF$_2$CF(CF$_3$)O)$_{b4}$— (R$_f$-IIB)

wherein:
b1, b2, b3, b4, are independently integers≥0 such that the number average molecular weight is between 400 and 10,000, preferably between 400 and 5,000; preferably b1 is 0, b2, b3, b4 are >0, with the ratio b4/(b2+b3) being ≥1;

—(CF$_2$CF$_2$O)$_{c1}$(CF$_2$O)$_{c2}$(CF$_2$(CF$_2$)$_{cw}$CF$_2$O)$_{c3}$— (R$_f$-IIC)

wherein:
cw=1 or 2;
c1, c2, and c3 are integers≥0 chosen so that the number average molecular weight is between 400 and 10,000, preferably between 400 and 5,000; preferably c1, c2 and c3 are all >0, with the ratio c3/(c1+c2) being generally lower than 0.2;

—(CF$_2$CF(CF$_3$)O)$_d$— (R$_f$-IID)

wherein:
d is an integer>0 such that the number average molecular weight is between 400 and 10,000, preferably between 400 and 5,000;

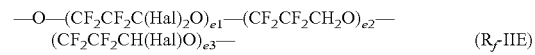
(R$_f$-IIE)

wherein:
Hal, equal or different at each occurrence, is a halogen selected from fluorine and chlorine atoms, preferably a fluorine atom;
e1, e2, and e3, equal to or different from each other, are independently integers≥0 such that the (e1+e2+e3) sum is comprised between 2 and 300.

More preferably, chain R$_f$ complies with formula (R$_f$-III) here below:

—(CF$_2$CF$_2$O)$_{a1}$(CF$_2$O)$_{a2}$— (R$_f$-III)

wherein:
a1, and a2 are integers>0 such that the number average molecular weight is between 400 and 10,000, preferably between 400 and 5,000, with the ratio a2/a1 being generally comprised between 0.1 and 10, more preferably between 0.2 and 5.

Preferably, groups Y and Y', equal to or different from one another, are selected from any one of the followings:
—CFXCH$_2$O(CH$_2$CH$_2$O)$_n$H and —CF$_2$CF$_2$CH$_2$O(CH$_2$CH$_2$O)$_n$H, wherein X is F or CF$_3$ and n ranges from 0 to 5;
—CFXCH$_2$O(CH$_2$CHOHCH$_2$O)$_{n'}$H and —CF$_2$CF$_2$CH$_2$O(CH$_2$CHOHCH$_2$O)$_{n'}$H wherein X is F or CF$_3$ and n' ranges from 1 to 3.

More preferably, groups Y and Y', equal to or different from one another, are selected from —CF$_2$CH$_2$O(CH$_2$CH$_2$O)$_n$H, wherein n ranges from 0 to 2, and —CF$_2$CH$_2$OCH$_2$CHOHCH$_2$OH.

Particularly preferred PFPE (P$_{pol}$) of formula (II) are those in which chain R$_f$ is a chain of formula (R$_f$-III) as defined above and groups Y and Y', equal to or different from one another, are selected from —CF$_2$CH$_2$O(CH$_2$CH$_2$O)$_n$H, wherein n ranges from 0 to 2, and —CF$_2$CH$_2$OCH$_2$CHOHCH$_2$OH. Among this group of particularly preferred PFPE (P$_{pol}$) of formula (II), those having a molecular weight ranging from 400 to 3,000 are particularly preferred.

Still more preferred are the following PFPE (P$_{pol}$):
1) PFPE (P$_{pol}$)-(IIA), wherein R$_f$ is a chain of formula (R$_f$-III) as defined above and both groups Y and Y' comply with formula —CF$_2$CH$_2$O(CH$_2$CH$_2$O)$_n$H, wherein n is as defined above; preferably, n is 0 or ranges from 1 to 2 (in the following, (P$_{pol}$)-(IIA) will also be referred to as "PFPE diols IIA" or "(P$_{diol}$)-(IIA)");
2) PFPE (P$_{pol}$)-(IIB) wherein R$_f$ is a chain of formula (R$_f$-III) as defined above and both groups Y and Y' comply with formula —CF$_2$CH$_2$OCH$_2$CHOHCH$_2$OH (in the following also referred to as "PFPE tetraol (IIB)" or "(P$_{tetraol}$)-(IIB)".

As indicated above, one or more PFPE (P$_{pol}$) can be used in the process of the invention; the use of different PFPE (P$_{pol}$) allows modulating the lubricant properties, for instance the adhesion to the MRM surface, according to specific needs. For the purposes of the present invention, particularly preferred is the use of a mixture containing (P$_{diol}$)-(IIA), (P$_{tetra}$)-(IIB) and also a PFPE (P$_{pol}$)-(IIC), wherein R$_f$ is a chain of formula (R$_f$-III) as defined above and one of Y and Y' is a —CF$_2$CH$_2$OH group and the other one is a group of formula —CF$_2$CH$_2$OCH$_2$CHOHCH$_2$OH (in the following also referred to as "PFPE triol IIC" or "($P_{triol}$)-(IIC)". PFPE diols (IIA) are commercially available from Solvay Specialty Polymers Italy under the trade name Fomblin® Z-DOL and Fluorolink®; PFPE ($P_{tetraols}$)-(IIB) can be conveniently prepared through a process comprising the reaction of ($P_{diol}$)-(IIA) with glycerine of formula:

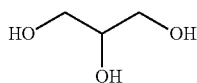

in an activated and protected form (herein after "APG"), followed by removal of the protective groups, as disclosed in EP 2197939 A (SOLVAY SOLEXIS SPA) 23 Jun. 2010, which is herein incorporated by reference. Protective groups and activating groups disclosed in EP 2197939 are preferred for the purposes of the present invention.

The procedure disclosed in EP 2197939 allows also to conveniently manufacture mixtures of PFPE ($P_{pol}$)-(IIA)-(IIC) to be used in the present invention if the reaction between ($P_{diol}$)-(IIA) and APG is not allowed to proceed until 100% conversion of the hydroxyl end groups of ($P_{diol}$)-(IIA) into the corresponding protected diol end groups. In particular, following the procedure of example 1 of EP 2197939, which comprises the reaction of the mesyl derivative of solketal [(2,2-dimethyl-1,3-dioxolan-4-yl) methanol] with a PFPE ($P_{diol}$)-(IIA) and by allowing the reaction to proceed until conversion lower than 100%, a mixture containing:

unreacted ($P_{diol}$)-(IIA)

PFPE ($P_{trio}$)-(IIC) wherein the two hydroxy group in the Y or Y' group of formula —$CF_2CH_2OCH_2CHOHCH_2OH$ are protected with an isopropylidene ketal and a PFPE polyol [PFPE ($P_{tetraol}$)-(IIB)] wherein the two hydroxy groups in the Y and Y' groups of formula —$CF_2CH_2OCH_2CHOHCH_2OH$ are protected with an isopropylidene ketal.

Mixtures of PFPE polyols (IIA)-(IIC) can be used in the process of the invention either in the protected or in the unprotected form. In the former case, protected ($P_{pol}$) (IIA)-(IIC) are directly treated with a base as described below to provide the corresponding mixture (M); the protective groups can be removed after obtainment of mixture (M2) and residual ($P_{pol}$) (IIA)-(IIC) can be removed in step 5). Alternatively, when they are used in the unprotected form, the protective groups are removed before the preparation of mixture (M).

For the sake of accuracy, it is pointed out that all PFPE ($P_{pol}$) of formula (II) may still include a small percentage of the corresponding mono-functional PFPE alcohol, i.e. a PFPE alcohol where one chain end is a non-functional end group and the other one is a group Y or Y' as defined above. Examples of non-functional end-groups are those complying with formula $C_xHal_{(2x+1-y)}H_y$, where x ranges from 0 to 4 and Hal is selected from F, Cl, Br; preferred examples of such groups are —$CF_3$, —$C_2F_5$, $C_3F_8$, —$CF_2H$, —$CF_2CF_2H$; generally, non-functional end groups are present in an amount lower than 10%, preferably lower than 5% by mol with respect to the overall amount of end groups. This small amount of non-functional end groups decreases the functionality of the PFPE ($P_{pol}$). Although non-functional PFPE, i.e. PFPE having non-functional groups at both chain ends, may also be contained in ($P_{pol}$), their amount is usually negligible and does not have an impact on the functionality of ($P_{pol}$). Throughout the present description, any reference to a ($P_{pol}$) of formula (II) is meant to comprise also such a small percentage of the corresponding mono-functional PFPE alcohol and non-functional PFPE.

Definition of PFPE (Palk)

PFPE ($P_{alk}$) is a PFPE ($P_{pol}$) wherein at least one hydroxy group is salified.

Perhalocyclophosphazenes (CPhalo)

Perhalocyclophosphazene ($CP_{halo}$) suitable for carrying out the process of the invention comply with formula (I) here below:

wherein Hal represents a halogen selected from fluorine, chlorine, bromine and iodine, preferably chlorine, and z is an integer ranging from 3 to 7. Preferably, ($CP_{halo}$) complies with formula (I-A) or (I-B) here below:

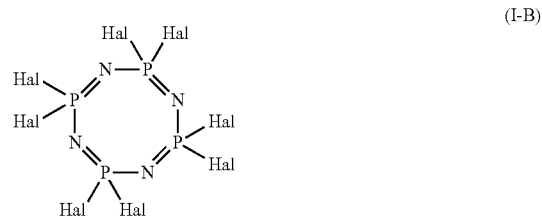

wherein Hal is as defined above.

In the process of the invention, it is possible to use mixtures of more perhalocyclophosphazenes ($CP_{halo}$), in particular mixtures of ($CP_{halo}$) (I-A) and (I-B) as defined above. However, it is preferred to use only one ($CP_{halo}$); particularly preferred is the use of a ($CP_{halo}$) of formula (I-A); more preferably, ($CP_{halo}$) (I-A) is hexachlorocylophosphazene.

Perhalocyclophosphazenes ($CP_{halo}$) (I-A) and (I-B) are commercially available and can be obtained, for example, from Strem Chemicals, Inc.

DETAILED DESCRIPTION OF THE PROCESS OF THE INVENTION

The process of the invention is typically carried out as described herein below.

Step 1—Preparation of Mixture (M)

Mixtures (M) are typically prepared by treating a PFPE ($P_{pol}$) with a base, usually a strong inorganic base, preferably NaOH or KOH, more preferably KOH, or an organic base, preferably potassium tert-butylate, in an equivalent amount ranging lower than 30%, preferably ranging from 5 to 15%, with respect to PFPE ($P_{pol}$). Typically, a water solution of inorganic base having a concentration of about 50% wt is added to PFPE ($P_{pol}$) and the resulting mixture is heated until complete elimination of water. Usually, the temperature is of about 70° C., but it can be adjusted by the person skilled in the art according to the selected PFPE ($P_{pol}$) and base. In the present description, the expression "an equivalent amount of base" means the equivalents of the base referred to the total equivalents of hydroxy groups of the PFPE ($P_{pol}$).

Step 2—Preparation of Mixture (M1)

A perhalocyclophosphazene ($CP_{halo}$) (I-A) and/or (I-B) is dissolved in a fluorinated aprotic polar solvent, which is typically selected from hydrofluoroethers (HFEs), like 3M™ Novec™ HFEs, hydrofluorocarbons (HFCs) and hexafluoroxylene, the preferred solvent being hexafluoroxylene. The kind and amount of solvent will be selected by the skilled person according to the selected ($CP_{halo}$); however, the amount of solvent is typically adjusted in such a way as that the concentration of ($CP_{halo}$) ranges from 1 to 10% w/w.

For the sake of clarity, it is pointed out that the term "equivalent" referred to perhalocyclophosphazenes ($CP_{halo}$) is referred to P—Cl groups therein contained. Thus, 1 mol of perhalocyclophosphazenes ($CP_{halo}$)-(IA) contains six equivalents of P—Cl groups, while 1 mol of perhalocyclophosphazenes ($CP_{halo}$)-($I_B$) contains 8 equivalents of P—Cl groups. In order to obtain cyclophosphazene derivatives wherein each P atom in the phosphazene ring bears two PFPE substitutents, the equivalent ratio between (PFPE-$P_{alk}$) and ($CP_{halo}$) must be of at least of 1; this means that if ($CP_{halo}$) (IA) is used, the molar ratio between the PFPE-$P_{alk}$ and ($CP_{halo}$) (IA) must be at least 6; if ($CP_{halo}$) (IB) is used, the molar ratio between the PFPE-$P_{alk}$ and ($CP_{halo}$) (IA) must be at least 8. However, it has been observed that, in order to optimise the reaction rate, it is preferred that the equivalent ratio of (PFPE-$P_{alk}$)/($CP_{halo}$) ranges from 1.1 to 2.5; an equivalent ratio of about 2 is particularly preferred. Indeed, it has been observed that when the process of the invention is carried out using an equivalent ratio of (PFPE-$P_{alk}$)/($CP_{halo}$) equal to 2 and a mixture (M) wherein the equivalent concentration of (PFPE-$P_{alk}$) in PFPE ($P_{pol}$) is between 10 and 15%, mixtures (M4) with an overall content of PFPE (CP-1), (CP2) and (CP3) of about 80% wt can be obtained in less than 10 hours.

According to a preferred embodiment (herein after "procedure A"), mixture (M) is stirred and heated at a temperature ranging from 40° C. to 90° C., then slowly added with the solution of ($CP_{halo}$), preferably (I-A) and/or (I-B), typically in about 2 to 6 hours.

According to another embodiment, (herein after "procedure B"), a solution of ($CP_{halo}$), preferably (I-A) and/or (I-B), is stirred and heated at a temperature ranging from 40° C. to 90° C., then slowly added with mixture (M).

According to another embodiment (herein after "procedure C"), mixture (M) and the solution of ($CP_{halo}$), preferably (I-A) and/or (I-B), are rapidly mixed together at room temperature, to provide a mixture (M1) which is then heated to a temperature ranging from 40° C. to 90° C.

Among procedures A-C, procedure A is preferred.

Step 3—Preparation of Mixture (M2)

After obtainment of mixture (M1) [i.e. once mixture (M) is contacted with all the solution of ($CP_{halo}$)], the fluorinated aprotic polar solvent is optionally removed, typically by evaporation under vacuum, then the mixture is stirred and heated until complete conversion of the P—Cl groups of ($CP_{halo}$) into P—OCH$_2$— groups. Typically, conversion is checked by withdrawing samples and by submitting them to $^{31}$P-NMR spectroscopy; complete conversion (99% conversion) is confirmed by the appearance of a singlet at 17 ppm.

Step 4—Preparation of Mixture (M3)

Once complete conversion is achieved, the resulting mixture (M2) is submitted to hydrolysis, namely acid hydrolysis. Typically, hydrolysis is accomplished by addition of aqueous HCl and an aliphatic alcohol, typically isobutyl alcohol. The aqueous phase is then separated to provide an organic phase which, after drying and removal of solvent(s), affords mixture (M3). Mixture (M3) comprises PFPE cyclophosphazene derivatives (CP-1)-(CP-4) as defined above in admixture with unreacted PFPE ($P_{pol}$), preferably a PFPE ($P_{pol}$) of formula (II) as defined above, in an amount typically ranging from 50 to 90% wt with respect to the weight of the mixture.

If a mixture of PFPE ($P_{pol}$) (IIA)-(IIC) is used in the protected form, the protective groups are completely removed according to known methods.

Mixtures (M3) obtainable according to the above steps 1)-4) are also part of the present invention. These mixtures can be used in cases where the lubrication of MRM is satisfactorily achieved at low concentrations of the PFPE cyclophosphazene derivatives of the invention, which still contain a certain amount of unreacted PFPE ($P_{pol}$) (IIA)-(IIC) ranging from 50 to 90% wt. Mixtures (M3) can be either used as such or they can be used in the preparation of further lubricant compositions.

Step 5) Preparation of Mixture (M4)

Mixture (M3) can optionally be submitted to distillation in order to remove the excess of PFPE ($P_{pol}$) to provide mixtures (M4), which comprises PFPE cyclophosphazene derivatives (CP-1)-(CP-4) as defined above in admixture with unreacted PFPE ($P_{pol}$), preferably a PFPE ($P_{pol}$) of formula (II) as defined above, said PFPE ($P_{pol}$) being in a lower amount than in mixture (M3); typically, in mixture (M4) the PFPE ($P_{pol}$) is in an amount ranging from 1 to 30% with respect to the weight of the mixture.

Mixtures (M4) obtainable through steps 1)-5) as defined above are also part of the present invention.

According to a preferred embodiment, mixtures (M3) and (M4) in accordance with the present invention are those obtainable from PFPE diols (II) as defined above and phosphazenes ($CP_{halo}$)-(IA) and/or (IB) as defined above.

Such mixtures thus comprise dangling cyclic phosphazenes (CP-1) complying with the formula here below:

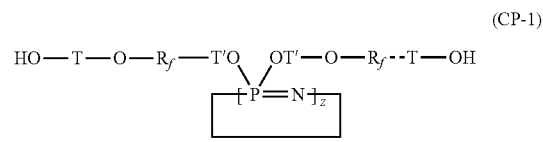

(CP-1)

wherein $R_f$ is a fluoropolyoxyalkylene chain as defined above, z is 3 or 4 and T and T', equal to or different from one another, represent a hydrocarbon group which is optionally fluorinated and which optionally contains one or more heteroatoms and/or one or more hydroxy groups. Preferably, T and T', equal to or different from one another, are chosen is such a way as T-O and T-O' are any one of the followings: —CFXCH$_2$O(CH$_2$CH$_2$O)$_n$, —CFXCH$_2$O(CH$_2$CHCH$_3$O)$_n$ and —CF$_2$CF$_2$CH$_2$O(CH$_2$CH$_2$O)$_n$, wherein X is F or CF$_3$ and n ranges from 0 to 5;

—CFXCH$_2$O(CH$_2$CHOHCH$_2$O)$_{n'}$ and —CF$_2$CF$_2$CH$_2$O (CH$_2$CHOHCH$_2$O)$_{n'}$, wherein X is F or CF$_3$ and n' ranges from 1 to 3.

Particularly preferred are mixtures (M3) and (M4) obtainable by using ($CP_{halo}$)-(IA), preferably hexachlorocyclophosphazene, with a PFPE diol (IIA) or with a mixture of PFPE ($P_{pol}$) (IIA)-(IIC) as defined above. Thus, these mixtures contain a dangling cyclic phosphazenes of formula (CP-1) wherein n is 3 and groups T-O and T'-O, equal to or different from one another, are selected from —$CF_2CH_2O$ ($CH_2CH_2O)_n$ and —$CF_2CH_2OCH_2CHOHCH_2O$, wherein n is as defined above; preferably, n ranges from 0 to 2.

Most particularly preferred are mixtures (M3) and (M4) obtainable using a ($CP_{halo}$)-(IA), preferably hexachlorocyclophosphazene, and a PFPE diol (IIA) as defined above, wherein both Y and Y' are —$CF_2CH_2O(CH_2CH_2O)_nH$, wherein n is as defined above. Thus, these mixtures contain a dangling cyclic phosphazenes (CP-1) wherein z is 3 and groups T-O and T'-O are both —$CF_2CH_2O(CH_2CH_2O)_n$, wherein n is as defined above.

Most particularly preferred are also mixtures (M3) and (M4) obtainable using a ($CP_{halo}$)-(IA), preferably hexachlorocyclophosphazene, and a protected mixture of PFPE ($P_{pol}$) (IIA)-(IIC) as defined above. These mixtures (M3) and (M4) contain a dangling cyclic phosphazenes (CP-1) wherein z is 3 and groups T-O are independently selected from —$CF_2CH_2O(CH_2CH_2O)_n$ wherein n is as defined above, and —$CF_2CH_2OCH_2CHOHCH_2O$, while groups T'-O are —$CF_2CH_2O(CH_2CH_2O)_n$ wherein n is as defined above.

Mixtures (M3) and (M4) typically contain, in addition to the desired dangling PFPE (CP-1), also spiro-, ansa- and bridged hydroxy-PFPE cyclophosphazenes [herein after also respectively referred to as PFPE (CP-2), PFPE (CP-3) and PFPE (CP-4)], complying with the formulae reported here below:

in admixture with unreacted PFPE ($P_{pol}$), preferably a PFPE ($P_{pol}$)-(II). Mixtures (M4) can be used as such in the lubrication of MRM or for the preparation of lubricant compositions or they can be submitted to fractionation, including, but not limited to, fractionation with chromatographic techniques, solvent extraction techniques, and fractionation with a supercritical fluid, as described in detail herein below.

In particular, the applicant observed that any residual amount of PFPE ($P_{pol}$)-(II) can be removed by fractionation of a mixture (M4) with a supercritical fluid, namely supercritical $CO_2$ ($scCO_2$) and that this technique allows separating bridged PFPE (CP-4) from PFPE (CP1), (CP2) and (CP3), thereby obtaining a mixture [mixture (M5)] with reduced polydispersity.

Therefore, a further aspect of the present invention is a method for purifying a mixture (M4) containing a PFPE cyclophosphazene derivative [PFPE (CP-1)] wherein each phosphorus atom of the phosphazene ring bears two PFPE chains, each PFPE chain bearing at least one hydroxy group, said method comprising submitting mixture (M4) to fractionation, preferably to fractionation with a supercritical fluid, more preferably to fractionation with $scCO_2$.

In particular, a further aspect of the invention is a method comprising, preferably consisting of, steps 1)-5) as defined above, followed by a step 6) comprising, preferably consisting of, the fractionation of mixture (M4), preferably fractionation with a supercritical fluid, more preferably fractionation with $scCO_2$.

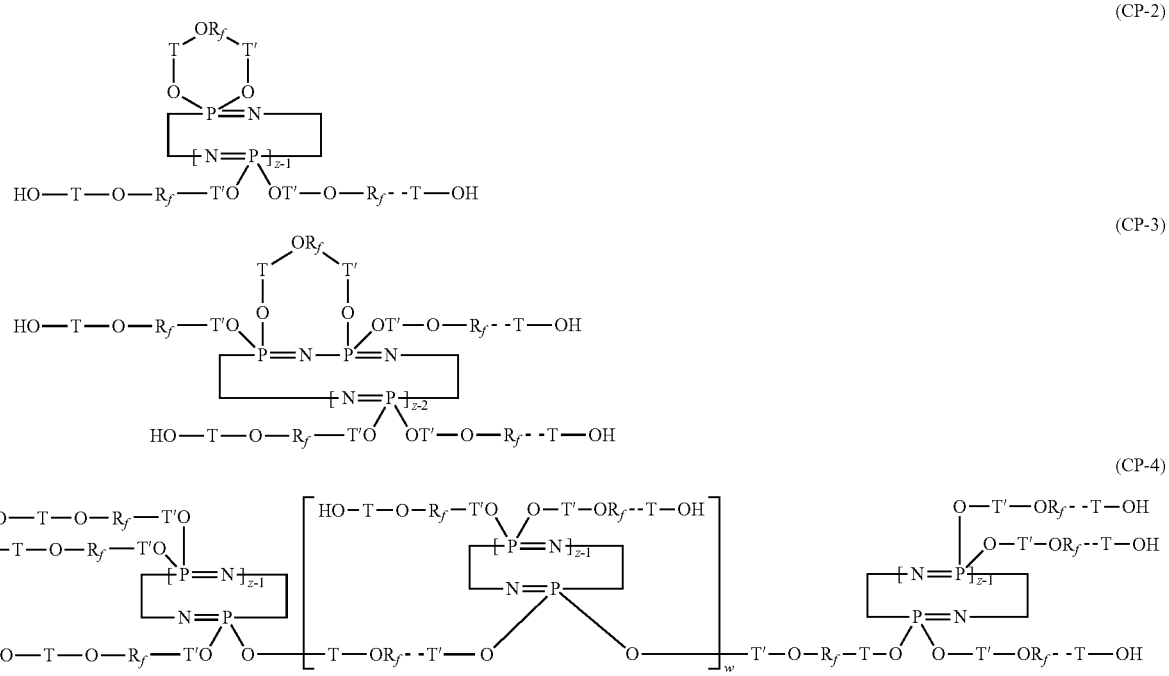

wherein $R_f$, z, w, T and T' are as defined above.

As explained in step 4) above, mixtures (M3) contains an amount of PFPE ($P_{pol}$), preferably a PFPE ($P_{pol}$)-(II) typically ranging from 50% to 90% wt. Mixtures (M4) still contain a residual amount of PFPE ($P_{pol}$), preferably a PFPE ($P_{pol}$)-(II), typically ranging from 1% to 30% wt. Therefore, mixtures (M3) and (M4) both comprise PFPE (CP-1)-(CP-4)

Fractionation with $scCO_2$ is typically carried out according to conventional methods under isothermal conditions, progressively increasing the pressure. Typically, temperature is set at a value ranging from 40° C. to 150° C., while pressure is progressively increased from 8 to 50 MPa.

Fractionation with $scCO_2$ allows to completely remove from mixture (M4) residual PFPE ($P_{pol}$) and also to obtain a mixture [mixture (M5)] with an increased amount of dangling, spiro and ansa PFPE (CP-1), (CP-2) and (CP-3) with respect to the corresponding bridged PFPE (CP-4). As it will be clearer from the results reported in the experimental section, any residual PFPE ($P_{pol}$) is eluted first, followed by fractions containing PFPE (CP-1), (CP-2) and (CP-3) (herein after "intermediate fractions"); PFPE (CP-4) is eluted last. Among the intermediate fractions, those which are eluted first contain a higher amount of PFPE (CP-2) and (CP-3), while those eluted last contain a higher amount of dangling PFPE (CP-1). All intermediate fractions can be pooled together and used as such; otherwise, only intermediate fractions containing a higher amount of dangling PFPE (CP-1) can be pooled together and, optionally, be re-submitted to fractionation with supercritical fluid in order to further increase purity; this process can be repeated as many times as desired in order to increase purity according to the intended use. Bridged PFPE (CP-4), which can be isolated by fractionation of mixture (M4), is also encompassed in the scope of the present invention.

Mixtures (M5), which contain dangling PFPE (CP-1) together with PFPE spiro- and ansa-PFPE (CP-2) and (CP-3), obtainable by means of the above purification method, in particular mixtures obtainable through a process comprising steps 1)-6) as defined above, are also within the scope of the present invention. These mixtures are characterised by a molar content of PFPE (CP-1) of at least 40%.

Preferred are mixtures (M5) obtainable from PFPE diols (II) as defined above and phosphazenes ($CP_{halo}$)-(IA) and/or (IB) as defined above.

Particularly preferred are mixtures (M5) obtainable from ($CP_{halo}$)-(IA), preferably hexachlorocyclophosphazene, and a PFPE diol (IIA) or with a mixture of PFPE ($P_{pol}$) (IIA)-(IIC) as defined above.

More particularly preferred are mixtures (M5) obtainable from ($CP_{halo}$)-(IA), preferably hexachlorocyclophosphazene, and a PFPE diol (IIA) PFPE diol (IIA) wherein both Y and Y' are —$CF_2CH_2O(CH_2CH_2O)_nH$, wherein n is as defined above.

More particularly preferred are also mixtures (M5) obtainable from ($CP_{halo}$)-(IA), preferably hexachlorocyclophosphazene, and a protected mixture of PFPE ($P_{pol}$) (IIA)-(IIC) as defined above.

Mixtures (M3)-(M5) according to the present invention can be used as such in the lubrication of MRM or they can be added with further ingredients and/or additives to provide further lubricant compositions for MRM. Thus, a further object of the present invention is a method for lubrifying MRM comprising using any one of mixtures (M3)-(M5) as defined above, alone or in the form of compositions containing further ingredients and/or additives. Particularly preferred is the use of mixtures (M4) and (M5), the use of mixtures (M5) being particularly preferred.

The invention will be illustrated in greater detail in the following experimental section.

Should the disclosure of any patents, patent applications, and publications which are incorporated herein by reference conflict with the description of the present application to the extent that it may render a term unclear, the present description shall take precedence.

EXPERIMENTAL SECTION

Material and Methods

Materials

PFPE ($P_{pol}$)-(IIA) used in example 1 was obtained by multiple thin layer distillations under vacuum of a commercial grade of Fomblin® Z-DOL PFPEs, until obtainment of a PFPE ($P_{pol}$) having EW=541, a1/a2=1.0, a1 and a2 being selected in such a way as to obtain Mn=1040, and Mw/Mn=1.10.

PFPE ($P_{pol}$)-(IIA) used in example 2, was obtained by multiple thin layer distillation under vacuum of commercial Fluorolink® E10H PFPE, until obtainment of a PFPE ($P_{pol}$) having EW=621, a1/a2=0.9, a1 and a2 being selected in such a way as to obtain Mn=1224 and Mw/Mn=1.10.

The mixture of PFPE polyols ($P_{pol}$) (IIA)-(IIC) used in example 3 was prepared from the PFPE ($P_{pol}$)-(IIA) used in example 1 following the procedure described in example 1 of EP 2197939, with the difference that conversion was limited to 30%, so as to obtain a mixture of diol (IIA), ketal-protected PFPE triol (IIB) and ketal-protected tetraol (IIC) having a hydroxyl equivalent weight of 773 g/eq.

Hexachlocyclotriphosphazene (HCP) was purchased from Strem

Chemicals Inc. with a 98.5% purity.

1,3-hexafluoroxylene was obtained from Miteni SpA.

HCl, NaOH 50% and isobutyl alcohol were reagent grade chemicals and they were used as received.

Analytical Methods

NMR Spectroscopy

All NMR experiments were recorded on an Agilent System 500 operating at 499.86 MHz for $^1H$ and 470.30 MHz for $^{19}F$ and equipped with a 5-mm triple resonance $^1H$, $^{19}F\{^{13}C,^{31}P\}$ PFG Agilent probe with a single axis (Z) gradient coil. Samples have been acquired either neat either dissolved in a mixture 3:1 v/v CFC113/Methanol-d4 ($CD_3OD$) 99.9 atom % D at about 10% w/w. Fluorine spectra have been referenced against external $CFCl_3$, phosphorous spectra against external $H_3PO_4$, whereas proton and carbon spectra has been referenced with respect to the residual solvent signal (Methanol-d4) at 3.3 ppm and 49.0 ppm respectively.

19F-NMR. The following fluorine acquisition parameters were applied on the neat samples: sample temperature of 25° C., sample spinning rate of 20 Hz, relaxation delay of 6.0 s, 90° flip angle corresponding to a pulse duration of 9.2 ms, at least 256 transients, and 65536 complex free induction decay (FID) data points acquired over a spectral width of 96153 Hz (acquisition time 0.6 s). Prior to Fourier transformation, all time domain data were processed with an exponential window function using a line broadening factor of 2 Hz.

1H-NMR. The following proton acquisition parameters were applied on the dissolved samples: sample temperature of 25° C., sample spinning rate of 20 Hz, relaxation delay of 20.0 s, 90° flip angle corresponding to a pulse duration of 9.0 ms, at least 64 transients, and 16384 complex free induction decay (FID) data points acquired over a spectral width of 8013 Hz (acquisition time 2.05 s). No weighting functions were applied.

31P-NMR. The following phosphorous acquisition parameters were applied on the neat samples: sample temperature of 25° C., sample spinning rate of 20 Hz, relaxation delay of 15.0 s, 90° flip angle corresponding to a pulse duration of 14.8 ms, at least 64 transients, and 16384 complex free induction decay (FID) data points acquired over a spectral width of 19841 Hz (acquisition time 0.83 s). Proton decoupling (WALTZ-16 scheme) was also applied during acquisition to cut out all possible $^1H$-$^{31}P$ coupling constant. Prior to Fourier transformation, all time domain data were processed with an exponential window function using a line broadening factor of 2 Hz.

13C-NMR. The following carbon acquisition parameters were applied on the dissolved samples: sample temperature of 25° C., sample spinning rate of 20 Hz, relaxation delay of 0.1 s, 45° flip angle corresponding to a pulse duration of 5.95 ms, at least 10000 transients, and 32768 complex free induction decay (FID) data points acquired over a spectral width of 31250 Hz (acquisition time 1.05 s). No weighting functions were applied. Proton decoupling (WALTZ-16 scheme) was also applied during the whole sequence acquisition to cut out all $^1$H-$^{13}$C coupling constant and increase peak intensity due to de nOe. Prior to Fourier transformation, all time domain data was processed with an exponential window function using a line broadening factor of 2 Hz.

Definition and Determination of the Ratio R

R is defined as the ratio between =P—OCH$_2$— groups (P is the phosphorus atom in the cyclophosphazene ring) and the overall amount of functional and non-functional end groups. In pure dangling PFPE (CP-1) R is 1, while in spiro-, ansa- and bridged-PFPE (CP-2), (CP-3) and (CP-4), the ratio is higher than 1.

The estimation of the ratio R has been performed by using proton, carbon and optionally fluorine spectra which show distinct peaks for =POCH$_2$— and free hydroxy groups.

4.4.2 Gel Permeation Chromatography (GPC)

Molecular weight distribution, Mn and Mw averages and polydispersity were determined by Gel Permeation Chromatography (GPC).

The GPC system was equipped with a Waters HPLC 515 pump, three PL-Gel columns (one Mixed-D and two Mixed-E) and a Waters 2414 refractive index detector. The columns and detector were thermostated at 35° C.

The mobile phase was a mixture of 1,3-bis(trifluoromethyl)benzene and isopropanol (80/20 vol.), fluxed at 1.0 ml/min. Samples were dissolved at 1% wt/vol concentration in the mobile phase under stirring at room temperature until complete dissolution (about 1 hour). For the analysis 200 ml of the solution were injected.

The calibration curve was obtained by using seven Fomblin® Z DOL PFPE narrow fractions with molecular weights known from NMR analysis and falling in the range 460-9200. Acquisition and the calculations were performed using Waters Empower software.

EXAMPLES

Example 1

Manufacture of a Mixture (M4) From a PFPE Diol (IIA) and Hexachlorocyclophosphazene and Fractionation by scCO2

Step 1—Mixture (M)

540 g of PFPE diol (IIA) of formula:

HO—CH$_2$CF$_2$O(CF$_2$CF$_2$O)$_{a1}$(CF$_2$O)$_{a2}$CF$_2$CH$_2$—OH (EW 541 g/eq; 998.15 meq.) was charged into a 1 l round-bottomed flask equipped with mechanical stirrer, dropping funnel, thermometer and refrigerant, then added with 14.84 g KOH (132.26 meq.; 50% solution in water). The mixture was heated and maintained at 80° C. under stirring, then vacuum was applied by means of a mechanical pump until complete elimination of water (about 2 hours at P=10 Pa), thereby obtaining a clear solution.

Step 2)—Mixture (M1)

In a separated flask 3.50 g hexachlorocyclotriphosphazene (HCP, 60.40 meq.) was dissolved under nitrogen atmosphere in 108 g 1,3-hexafluoroxylene (HFX); the solution was poured into the dropping funnel and slowly added to the solution from step 1) under stirring at 80° C. during 5 hours.

Step 3)—Mixture (M2)

HFX was then distilled under vacuum and the reaction mixture from step 2) was maintained at 80° C. under stirring, controlling the conversion from time to time by $^{31}$P-NMR analysis. After about 2 hours the conversion was quantitative (singlet in the $^{31}$P-NMR at 17 ppm) and the reaction was stopped.

Step 4)—Mixture (M3)

After cooling, mixture (M2) was added with 140 g distilled water, 16 g HCl 37% w/w water solution and 23 g isobutyl alcohol. The resulting two phases were vigorously stirred at 50° C. for 30 minutes and, after separation, the lower organic layer was collected. The solvents (isobutanol and traces of water) were removed by distillation at 80° C. under reduced pressure to afford 534 g crude product, containing a large amount of unreacted PFPE diol (IIA).

Step 5)

Most of diol (IIA) was then removed by molecular distillation under a residual pressure of 1.8 Pa (two stages at 120° C. and 150° C. respectively), obtaining two low-viscous fractions (61% and 25% by weight, respectively) of substantially pure PFPE diol (IIA), as confirmed by the absence of signals in the $^{31}$P-NMR spectrum. The high boiling residue (74.8 g) was characterized by $^{19}$F-NMR, $^1$H-NMR, $^{31}$P-NMR and GPC analysis.

The GPC chromatogram shows three main components having a peak molecular weight of 1836, 6539 and 10995 dalton respectively. The first component corresponds to residual PFPE diol (IIA), the second component is attributed to dangling-, spiro- and ansa-PFPE (CP-1), (CP-2) and (CP-3), while the last component is most likely attributed to a bridged PFPE (CP-4).

Step 6—Fractionation of Mixture (M4) With scCO2—Obtainment of Mixture (M5)

Mixture (M4) obtained from step 5 was charged into a 300 ml SFT-150 Supercritical CO$_2$ Extraction System and heated at 100° C. Through a step-by-step pressure increase (from 18 to 30 MPa) and operating at a CO$_2$ flow rate of 4 Nl/min, 13 fractions were collected. Each fraction was characterized by $^{31}$P-NMR, $^{19}$F-NMR, $^1$H-NMR, $^{13}$C-NMR and GPC. The GPC analysis of the fractions shows that residual PFPE diol (IIA) and bridged PFPE (CP-4) were selectively removed at lower and higher pressures respectively. Fractions 3 to 9 (33.9 g), containing only PFPE (CP-1), (CP-2) and (CP-3), were separately washed three times with water/isobutyl alcohol and after phase separation residual solvents were carefully removed. The GPC analyses of fractions 3 to 9 showed in all cases a single peak having average molecular weight Mn of about 5900 and confirm the absence of PFPE diol (IIA) and bridged PFPE (CP-4).

NMR analyses confirmed the structure of the PFPE (CP-1)-(CP-3);

particularly significant are the signals corresponding to P—OCH$_2$CF$_2$O— moieties: $^{19}$F—: −78.8, −80.8 ppm; $^1$H—: 4.31 ppm; $^{13}$C—: 65.5 ppm (—CH$_2$) and those corresponding to —CF$_2$CH$_2$OH moieties: $^{19}$F—: −81.1, −83.1 ppm; $^1$H—: 3.80 ppm; $^{13}$C—: 63.0 ppm (—CH$_2$). The ratio R between the P—OCH$_2$ CF$_2$O— and the —OCF$_2$X end groups (X=—CH$_2$OH, —F or —H, measured by $^{19}$F-NMR, $^1$H-NMR and $^{13}$C-NMR) was found to be higher than 1 in all fractions, indicating that the product is a mixture (M4) of dangling PFPE (CP-1) and spiro- and ansa-PFPE (CP-2) and (CP-3).

From the R ratio it is possible to calculate the composition of each fraction, which is reported in Table 1.

TABLE 1

| Fraction number | R | Molar composition (%) | |
|---|---|---|---|
| | | (CP-1) | (CP-2)/(CP-3) |
| 3 | 1.24 | 43 | 57 |
| 4 | 1.20 | 50 | 50 |
| 5 | 1.18 | 54 | 46 |
| 6 | 1.14 | 63 | 37 |
| 7 | 1.13 | 66 | 34 |
| 8 | 1.10 | 73 | 27 |
| 9 | 1.07 | 79 | 21 |

The above data indicate that it is possible to increase the amount of PFPE (CP-1) with respect to PFPE (CP-2) and (CP-3) by fractionation with scCO$_2$. An even further increase can be achieved by collecting the fractions with a higher content of (CP-1) and submitting the same to further scCO$_2$ fractionation cycles.

Example 2

Manufacture of a Mixture (M4) From a PFPE Diol (IIA) and Hexachlorocyclophosphazene and of a Mixture (M5) by Fractionation with scCO2

Step 1—Mixture (M)
188 g of an ethoxylated PFPE diol of formula:

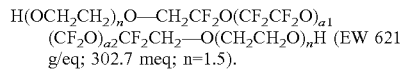
(CF$_2$O)$_{a2}$CF$_2$CH$_2$—O(CH$_2$CH$_2$O)$_n$H (EW 621 g/eq; 302.7 meq; n=1.5).

were charged into a 0.5 l round-bottomed flask equipped with a mechanical stirrer, a dropping funnel, a thermometer and a refrigerant, and then added with 8.85 g KOH (78.9 meq; 50% solution in water). The mixture was heated and maintained at 80° C. under stirring, then vacuum was applied to the reactor by means of a mechanical pump until complete elimination of water (about 30 minutes at P=4 Pa), to obtain homogeneous, slightly opalescent solution.

Step 2—Mixture (M1)
In a separated flask 2.11 g hexachlorocyclotriphosphazene (HCP, 36.4 meq.) was dissolved in 53 g 1,3-hexafluoroxylene (HFX); the resulting solution was poured into the dropping funnel and slowly added to mixture (M) from step 1), under stirring at 80° C. during 2 hours.

Step 3—Mixture (M2)
HFX was then distilled off under vacuum and the reaction mixture was maintained at 80° C. under stirring controlling the conversion from time to time by $^{31}$P-NMR analysis. After 30 minutes the conversion was quantitative (singlet in the $^{31}$P-NMR spectrum at 17 ppm) and the reaction was stopped.

Step 4)—Mixture (M3)
After cooling at room temperature, the mixture was added with 170 g distilled water, 11 g HCl 37% w/w solution in water and 34 g isobutyl alcohol. The two phases were vigorously shaken and, after separation, the lower organic layer was collected and the solvents were removed by distillation at 80° C. under reduced pressure to afford 182 g crude product, which contains unreacted ethoxylated PFPE diol and a mixture of dangling, spiro, ansa and bridged PFPE complying with formulae (CP-1)-(CP-4) wherein R$_f$ is (CF$_2$CF$_2$O)$_{a1}$(CF$_2$O)$_{a2}$, wherein p and q are as defined above and T-O and T'-O are both —O(CH$_2$CH$_2$O)$_n$— with n=1.5.

Step 5—Mixture (M4)
Most of the unreacted ethoxylated PFPE diol was removed in two passages by molecular distillation under a residual pressure of 2.2 Pa at 160° C. and 190° C., respectively. Two low-viscous fractions (54% and 19% by weight, respectively) of only ethoxylated PFPE diol, as confirmed by the absence of signals in the $^{31}$P-NMR spectrum, were removed, leaving 49 g of a high boiling, low volatility residue [mixture (M4)], which was characterized by $^{19}$F-NMR, $^1$H-NMR and $^{31}$P-NMR.

Step 6—Preparation of Mixture (M5) by Fractionation of Mixture (M4) With scCO2
Mixture (M4) from step 5) was charged into a 300 ml SFT-150 scCO$_2$ Extraction System and heated at 100° C. Through a step-by-step increase of pressure (from 20 to 35 MPa) and operating at a CO$_2$ flow rate of 4 Nl/min, dangling, spiro and ansa PFPE (CP1)-(CP3) were isolated. Any residual unreacted ethoxylated PFPE diol was easily removed at scCO$_2$ low pressure, while bridged PFPE (CP-4) was selectively collected at high pressure. Each fraction was characterized by $^{31}$P-NMR, $^{19}$F-NMR, $^1$H-NMR, $^{13}$C-NMR and GPC. Fractions containing only PFPE (CP1)-(CP3) were pooled (overall yield: 4 g). Ratio R, measured by $^{19}$F-NMR, $^1$H-NMR and $^{13}$C-NMR, was found to be 1.22, corresponding to a molar percent composition of 46% PFPE (CP-1) and 54% PFPE (CP-2)+(CP-3).

Example 3

Manufacture of a Mixture (M4) from a Protected Mixture of PFPE (P$_{pol}$) (IIA)-(IIC) Mixture and Hexachlorocyclophosphazene and Manufacture of a Mixture (M5) by Fractionation with scCO2

Step 1—Mixture (M)
635 g of ketal-protected mixture of PFPE (P$_{pol}$) (IIA)-(IIC) (EW=773, 821.5 meq) was charged into a 1 liter round bottom flask equipped with a mechanical stirrer, a dropping funnel, a thermometer and a refrigerant, and 22.36 g KOH (50% wt solution in water, 199.3 meq.) was added. The mixture was stirred and heated with an external bath to 80° C., then vacuum was applied by means of a mechanical pump until complete elimination of water (about half an hour).

Step 2—Mixture (M1)
In a separated flask 5.26 g hexachlorocyclotriphosphazene (90.77 meq) was dissolved in 164 g HFX; the solution was poured into the dropping funnel and slowly added to mixture (M) from step 1) under stirring at 80° C. during 3.5 hours.

Step 3—Mixture (M2)
The reaction mixture was maintained at 80° C. under stirring controlling the conversion from time to time by $^{31}$P-NMR analysis. After 30 minutes the conversion was quantitative (singlet in the $^{31}$P-NMR spectrum at 17 ppm) and the reaction was stopped.

Step 4—Hydrolysis and Deprotection to Obtain Mixture (M3)
The mixture was then added with 140 g distilled water, 21 g HCl 37% w/w water solution and 21 g isobutyl alcohol. The two phases were vigorously shaken for 1 h at 40° C. and, after separation, the lower organic layer was collected. The solvents (HFX and isobutyl alcohol) were removed by distillation at 80° C. under reduced pressure to afford 612 g of crude product.

The crude product was then added with 200 g methanol, 78 g distilled water and 37 g HCl 37% w/w water solution, and subsequently heated at 70° C. and stirred during 3 hours, in order to completely remove the protective groups. After phase separation, the lower organic layer was collected and the solvent was removed by distillation at 80° C. under reduced pressure, to afford 590 g crude product which was characterized by $^{31}$P-NMR, $^{19}$F-NMR and $^1$H-NMR.

Step 5—Mixture (M4)
Most of the unreacted precursors PFPE (P$_{pol}$) (IIA)-(IIC) were removed in two passages by molecular distillation under a residual pressure of 1.6 Pa at 180° C. and 200° C., respectively. Two fractions, corresponding to 81% by weight of only unreacted PFPE (P$_{pol}$) (IIA)-(IIC), as confirmed by the absence of signals in the $^{31}$P-NMR spectrum, were removed, leaving 112 g of a high boiling, low volatility residue, which was characterized by $^{19}$F-NMR, $^1$H-NMR, $^{31}$P-NMR and GPC.

Step 6—Preparation of Mixture (M5) by Fractionation of Mixture (M4) With scCO2
Mixture (M4) from step 5) was charged into a 300 ml SFT-150 scCO$_2$ Extraction System and heated at 100° C. Through a step-by-step increase of pressure (from 19.5 to 30 MPa) and operating at a CO$_2$ flow rate of 4 Nl/min, the dangling, spiro and ansa PFPE (CP1)-(CP3) were isolated.

Any residual unreacted PFPE ($P_{pol}$) (IIA)-(IIC) and tetraol (IIB) were easily removed at $scCO_2$ low pressure, while bridged PFPE (CP4) was selectively collected at high pressure. Each fraction was characterized by $^{31}$P-NMR, $^{19}$F-NMR, $^1$H-NMR, $^{13}$C-NMR and GPC. Fractions containing only PFPE (CP1)-(CP3) were pooled together (9.2 g). The ratio R between the P—$OCH_2CF_2O$— and the —$OCF_2X$ end groups (X=—$CH_2OH$, —$CH_2OCH_2CH(OH)CH_2OH$, —F or —H, measured by $^{19}$F-NMR, $^1$H-NMR and $^{13}$C-NMR) was found to be 1.21, corresponding to a molar percent composition of 48% (CP-1) and 52% (CP-2)+(CP-3). The ratio between —$CH_2OH$ and —$CH_2OCH_2CH(OH)CH_2OH$ end-groups resulted to be 1.34.

The invention claimed is:

1. A method of manufacturing cyclophosphazene derivatives, the method comprising:
   contacting a mixture (M), the mixture (M) comprising:
      a) a (per)fluoropolyether (PFPE) polyol [PFPE ($P_{pol}$)] comprising a fluoropolyoxyalkylene chain ($R_f$) having two chain ends, each chain end comprising at least one hydroxy group, and
      b) a corresponding alkoxide of said perfluoropolyether (PFPE) polyol [PFPE ($P_{alk}$)], wherein the equivalent concentration of PFPE ($P_{alk}$) in PFPE ($P_{pol}$) is lower than 30%
   with a perhalocyclophosphazene ($CP_{halo}$) to provide a mixture (M1) containing an equivalent ratio of PFPE ($P_{alk}$)/($CP_{halo}$) of at least 1;
   allowing mixture (M1) to react until complete disappearance of $P_{halo}$ groups to provide a mixture (M2);
   submitting mixture (M2) to hydrolysis to provide a mixture (M3);
   optionally removing PFPE ($P_{pol}$) from mixture (M3) to provide a mixture (M4).

2. The method according to claim 1 wherein PFPE ($P_{pol}$) complies with formula (II):

$$Y—O—R_f—Y' \qquad (II)$$

wherein $R_f$ is a fully or partially fluorinated polyoxyalkylene chain comprising repeating units R°, said repeating units being selected from the group consisting of:
   (i) —CFXO—, wherein X is F or $CF_3$,
   (ii) —CFXCFXO—, wherein X, equal or different at each occurrence, is F or $CF_3$, with the provision that at least one of X is —F,
   (iii) —$CF_2CF_2CW_2O$—, wherein each of W, equal or different from each other, are F, Cl, or H,
   (iv) —$CF_2CF_2CF_2CF_2O$—,
   (v) —$(CF_2)_j$—CFZ-O— wherein j is an integer from 0 to 3 and Z is a group of general formula —$OR_f'T_3$, wherein $R_f'$ is a fluoropolyoxyalkene chain comprising from 0 to 10 recurring units selected from: —CFXO—, —$CF_2CFXO$—, —$CF_2CF_2CF_2O$—, and —$CF_2CF_2CF_2CF_2O$—, with each of X being independently F or $CF_3$ and $T_3$ being a $C_1$-$C_3$ perfluoroalkyl group; and
Y and Y', equal to or different from one another, represent a hydrocarbon group containing at least one free hydroxy group, said hydrocarbon group being optionally fluorinated and/or optionally containing one or more heteroatoms.

3. The method according to claim 2 wherein Y and Y' are independently selected from:
   —$CFXCH_2O(CH_2CH_2O)_nH$, —$CFXCH_2O(CH_2CHCH_3O)_nH$, and —$CF_2CF_2CH_2O(CH_2CH_2O)_nH$, wherein X is F or $CF_3$ and n ranges from 0 to 5;
   —$CFXCH_2O(CH_2CHOHCH_2O)_{n'}H$ and —$CF_2CF_2CH_2O(CH_2CHOHCH_2O)_{n'}H$, wherein X is F or $CF_3$ and n' ranges from 1 to 3.

4. The method according to claim 2 wherein chain $R_f$ complies with formula ($R_f$-III):

$$—(CF_2CF_2O)_{a1}(CF_2O)_{a2}— \qquad (R_f\text{-III})$$

wherein a1 and a2 are integers>0 such that the number average molecular weight is between 400 and 10,000, with the ratio a2/a1 being comprised between 0.1 and 10; and
Y and Y', equal to or different from one another, are selected from:
   —$CFXCH_2O(CH_2CH_2O)_nH$ and —$CF_2CF_2CH_2O(CH_2CH_2O)_nH$, wherein X is F or $CF_3$ and n ranges from 0 to 5;
   —$CFXCH_2O(CH_2CHOHCH_2O)_{n'}H$ and —$CF_2CF_2CH_2O(CH_2CHOHCH_2O)_{n'}H$, wherein X is F or $CF_3$ and n' ranges from 1 to 3.

5. The method according to claim 4 wherein PFPE ($P_{pol}$) is a PFPE diol ($P_{diol}$) (IIA) wherein both Y and Y' comply with formula —$CF_2CH_2O(CH_2CH_2O)_nH$ wherein n ranges from 0 to 2.

6. The method according to claim 4 wherein PFPE ($P_{pol}$) is a mixture of:
   PFPE diol ($P_{diol}$) (IIA), wherein both Y and Y' comply with formula —$CF_2CH_2O(CH_2CH_2O)_nH$ wherein n ranges from 0 to 2;
   PFPE tetraol ($P_{tetraol}$)-(IIB), wherein both Y and Y' comply with formula —$CF_2CH_2OCH_2CHOHCH_2OH$ and
   PFPE triol ($P_{triol}$)(IIC), wherein one of Y and Y' is a group of formula $CF_2CH_2O(CH_2CH_2O)_nH$ wherein n ranges from 0 to 2 and the other of Y and Y' is a group of formula —$CF_2CH_2OCH_2CHOHCH_2OH$
   said mixture of PFPE ($P_{pol}$) (IIA)-(IIC) being optionally in the protected form.

7. The method according to claim 1 wherein perhalocyclophosphazene ($CP_{halo}$) is selected from one or more of perhalocyclophosphazene ($CP_{halo}$) complying with formula (I-A) or (I-B):

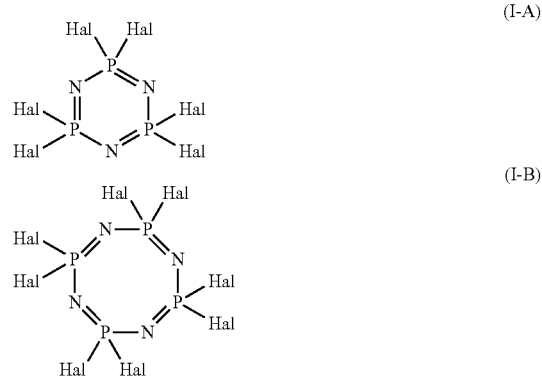

wherein Hal is a halogen selected from fluorine, chlorine, bromine and iodine.

8. The method according to claim 1 wherein the equivalent ratio of (PFPE-$P_{alk}$)/($CP_{halo}$) ranges from 1.1 to 2.5.

9. The method according to claim 8 wherein the equivalent ratio of (PFPE-$P_{alk}$)/($CP_{halo}$) is 2 and wherein the equivalent concentration of (PFPE-$P_{alk}$) in ($CP_{halo}$) is between 5% and 15%.

10. The method according to claim 1 further comprising submitting mixture (M4) to fractionation with a supercritical fluid.

11. A mixture of:
   (A) cyclophosphazene derivatives complying with formulae (CP-1)-(CP-4):

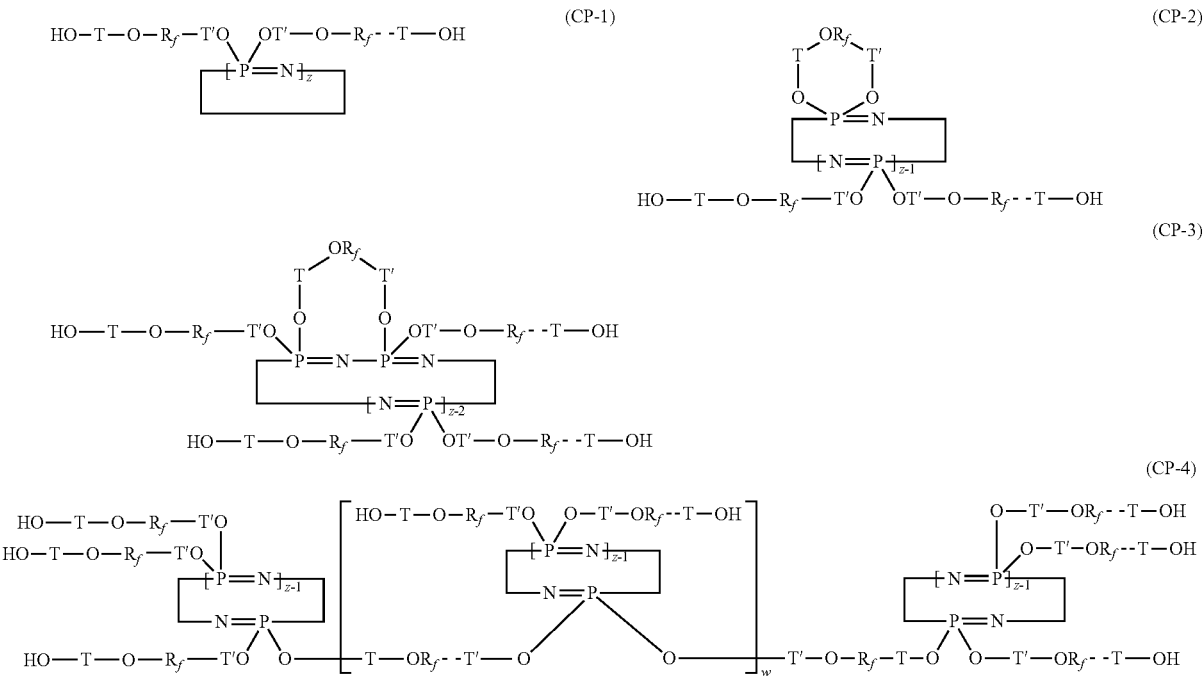

wherein $R_f$ is a fluoropolyoxyalkylene chain;
z is 3 or 4, w is selected from 0, 1 or 2; and
T and T', equal to or different from one another, represent a hydrocarbon group which is optionally fluorinated and which optionally contains one or more heteroatoms and/or one or more hydroxy groups, and (B) a PFPE ($P_{pol}$) of formula (II) as defined in claim 2.

12. The mixture of cyclophosphazene derivatives according to claim 11, wherein the mixture comprises the cyclophosphazene complying with formulae (CP-1)-(CP-3), characterised by a molar content of cyclophosphazene derivative (CP-1) of at least 40%.

13. A lubricant composition comprising a mixture of cyclophosphazene derivatives according to claim 11 in admixture with further ingredients or additives.

14. A method of lubrifying magnetic recording media comprising contacting the media with a lubricant composition as defined in claim 13.

15. The method according to claim 4 wherein a1 and a2 are integers>0 such that the number average molecular weight is between 400 and 5,000, with the ratio a2/a1 being comprised between 0.2 and 5.

* * * * *